US005273909A

United States Patent [19]

Piasio

[11] Patent Number: 5,273,909
[45] Date of Patent: Dec. 28, 1993

[54] IMMUNOASSAY FOR THE DETECTION OF SMALL ALIPHATIC ORGANIC COMPOUNDS

[75] Inventor: Roger Piasio, Cumberland, Me.

[73] Assignee: Quantix Systems, L.P., Cinnaminson, N.J.

[21] Appl. No.: 709,496

[22] Filed: Jun. 3, 1991

[51] Int. Cl.$^5$ .................. G01N 33/543; G01N 33/536
[52] U.S. Cl. .................. 436/518; 436/536; 436/547; 436/548; 436/124; 436/125; 436/126; 436/140; 436/822
[58] Field of Search ............. 436/518, 536, 547, 548, 436/124, 125, 126, 140, 822

[56] References Cited

FOREIGN PATENT DOCUMENTS 8603841 7/1986 World Int. Prop. O.
9010709 9/1990 World Int. Prop. O.

Primary Examiner—David Saunders
Assistant Examiner—Lora M. Green
Attorney, Agent, or Firm—Pennie & Edmonds

[57] ABSTRACT

Antibodies are raised against immunogens which include an aromatic ring moiety, preferably the compound 6-aminohexyl-p-tolylacetamide, which immunologically cross-react with small aliphatic organic compounds. These antibodies are useful in immunoassay methods for detecting a class of very small organic molecules such as 1,1-dihaloethylene and 1,1,2-trihaloethylene, whether alone or as a functional group on another molecule. Such antibodies and methods provide important tools for detecting significant environmental pollutants.

10 Claims, No Drawings

IMMUNOASSAY FOR THE DETECTION OF SMALL ALIPHATIC ORGANIC COMPOUNDS

FIELD OF THE INVENTION

This invention relates to the use of immunological methods for the detection of organic molecules. More particularly, it deals with the use of an antigen/antibody reaction between certain small organic molecules or with certain organic functional groups.

BACKGROUND OF THE INVENTION

The antigen/antibody reaction has long been known in the art. The highly specific nature of this reaction has led to its widespread application in both qualitative and quantitative asays. See, Skelly, D. S. et al. *Radioimmunoassays*, Clin. Chem., Vol. 19, pp. 146-86 (1973).

Stated in the most general terms, assay techniques which use the antigen/antibody reaction call for the "raising" of antibodies to an antigen, such as by injecting the antigen into the bloodstream of a rabbit or other suitable animal. The animal's immune system responds to the presence of the antigen by producing antibodies to the antigen. These antibodies are then harvested from the animal. The antibodies can be used in an assay procedure for the presence of the antigen (or the presence of its immunological equivalent) by mixing them with a sample which is thought to contain that compound.

This technique is not without it limitations. Among these is the difficulty which is encountered in raising antibodies to small molecules. Most small molecules fail to provoke an immune reaction (i.e. the production of antibodies) when they are introduced into the bloodstream of an animal. This is the case even though these compounds are often very toxic. It is believed that the mammalian immune system cannot "see" them and thus does not respond to them. Also, these molecules may be so very small that they cannot provide a sufficiently large "binding site" for antigen/antibody binding.

It is sometimes possible to surmount the first of these difficulties by attaching the molecule of interest to a larger molecule. In this case, the molecule of interest, which is called a hapten, is attached to a molecule such as bovine serum albumin (BSA) protein and then injected into the bloodstream of an animal. BSA is large enough to be "seen" by the immune system and the immune system reacts to the BSA and the hapten. This technique often result in the production of antibodies to the hapten. However, its effectiveness is not universal, and it has not been found to be effective in the production of antibodies to very small molecules or to specific small functional groups. This is thought to be because they are so small that antigen/antibody binding is difficult or impossible.

SUMMARY OF THE INVENTION

The present invention provides a means for the detection of a class of very small organic molecules by immunological methods. Specifically, 1,1-dihaloethylene and the 1,1-dihaloethylene functional group have been found to be capable of recognition by antibodies. Antibodies to these compounds can be raised and used to assay for their presence. This immunological phenomenon is even more pronounced where a third halogen atom is present, as in 1,1,2-trihaloethylene or the 1,1,2-trihaloethylene functional group.

DETAILED DESCRIPTION OF THE INVENTION

It has been found that antibodies can be raised which react specifically to compounds of the formula $CX_2=CX_aH_b$ (where X is a halogen, a is 0,1 or 2, and a+b=2) and to compounds which contain the $CX_2=CX_a$ functional group (where X is a halogen and a is 0 or 1). These compounds, functional groups and compounds which contain these functional groups shall hereinafter be referred to collectively by the term $CX_2=CX_a$, unless the context indicates otherwise.

Antibodies to $CX_2=CX_a$ can be raised by attaching it as a hapten to a larger molecule or by using an immunological crossreactant as a hapten. 6-aminohexyl-p-tolylacetamide has been found to be a highly effective crossreactant for the raising of antibodies to $CX_2=CX_a$. These antibodies can be used in qualitative and quantitative assays for commercially and environmentally important molecules such as trichloroethylene (TCE) and perchloroethylene (PCE).

1. Raising Antibodies

Antibodies to $CX_2=CX_a$ were raised in the following manner. An antigen was constructed in a conventional manner by linking a 6-aminohexyl-p-tolylacetamide hapten to BSA. This antigen was diluted in incomplete Freund's adjuvant, and injected into a rabbit. After 12 to 16 weeks, the animals were tested for the production of antibodies using the toluene as the reactant. Where a positive response was noted, production bleeds were conducted. Antibodies were then harvested in a conventional manner.

The antibodies so raised are known to react specifically to aromatic compounds such as benzene, toluene or xylene, as is described in the commonly assigned U.S. Pat. application of Piasio & Latt, Ser. No. 619,956, filed Nov. 30, 1990. However, it was not known that these antibodies could cross react with a very small organic molecule or functional group such as $CX_2=CX_a$. Indeed, it was neither known nor thought possible that such a molecule or functional group as $CX_2=CX_a$ could serve as a sufficient binding site for antigen/antibody binding.

2. Demonstration of Binding Reaction

The ability of aromatic compounds (such as toluene) to bind with these antibodies was demonstrated by a conventional competitive assay technique in which an enzyme conjugate capable of catalyzing a chromogenic reaction and which is known to bind to the antibodies was added to two tubes to which the antibodies had been immobilized. The antibodies in one tube were first exposed to toluene, those in the other tube were not. The toluene bound to the antibodies, thereby preventing or reducing binding between the antibodies and the enzyme conjugate. The amount of toluene which bound to the antibodies (and thus the amount of toluene in the sample) was quantitated by using a spectrophotometer to compare the amount of the chromogenic reaction which was found in each tube. This was expressed as a "sample to reference ratio" or "S/R ratio."

When trichloroethylene was tested for ability to bind with these antibodies, it was surprisingly discovered that there was a high degree of binding. Further tests were conducted with other compounds and the results of these tests are set forth in Table 1.

TABLE 1

| Compound | S/R Ratio | Conc. (ppm) |
| --- | --- | --- |
| Perchloroethylene | 0.35 | 20 |
| Trichloroethylene | 0.45 | 20 |
| trans - 1,2 dichloroethylene | 1.16 | 100 |
| trans - 1,2 dichloroethylene | 1.05 | 20 |
| 1,1,1 - trichloroethane | 1.0 | 20 |
| 1,2 - dichloroethane | 0.99 | 100 |
| Toluene | 0.22 | 20 |

From these and other tests conducted by the inventor, it became clear that $CX_2=CX_a$ compounds and functional groups are apparently capable of participation in antigen/antibody binding reactions. Compounds which contain the $CX_2=CX_a$ functional group present a specific recognition site to which antibodies to this functional group may bind. It has also been observed that this effect is strongest where a is 1 or 2.

It is possible to use TCE as a hapten and to raise antibodies to the $CX_2=CX_a$ group directly, rather than through a crossreactant.

The usefulness if this discovery will be readily appreciated by those skilled in the art. TCE, PCE and the other compounds which may be detected by this method are of great commercial and environmental importance. It is often necessary to control the presence of these compounds and to remove them from areas where they are present. The assay method provided by the present invention facilitates the detection of these compounds at concentrations which, though very low, are significant from an environmental, public health and regulatory point of view. Other uses and advantages of the invention will also be apparent to those skilled in the art.

I claim:

1. A method for detecting in a sample an antigen which is a first compound of the formula $$CX_2=CX_aH_b \qquad (I)$$

wherein
 X is a halogen;
 a is 0,1 or 2; and
 a+b=2,
or an antigen which is a second compound containing the functional group of the formula $$CX_2=CX_a-R \qquad (II)$$

wherein
 X is a halogen;
 a is 0 or 1; and
 R is the remainder of the second compound,
which method comprises the steps of:
 (a) producing an antibody which specifically binds to said first compound and said functional group of said second compound by immunization with an immunogen which includes as an antigenic determinant 6-aminohexyl-p-tolylacetamide;
 (b) contacting the antibody produced in step (a) with the sample; and
 (c) observing any binding of said antibody to said antigen in the sample,
wherein any such binding between said antibody and said antigen in the sample is indicative of the presence of said antigen.

2. A method according to claim 1 wherein a is not 0.
3. A method according to claim 1 wherein X is chlorine.
4. A method according to claim 2 wherein X is chlorine.
5. A method according to claim 1 wherein the first compound is trichloroethylene or perchloroethylene.
6. A method for detecting in a sample an antigen which is a first compound of the formula $$CX_2=CX_aH_b \qquad (I)$$

wherein
 X is a halogen;
 a is 0, 1 or 2; and
 a+b=2,
or an antigen which is a second compound containing the functional group of the formula $$CX_2=CX_a-R \qquad (II)$$

wherein
 X is a halogen;
 a is 0, or 1; and
 R is the remainder of the second compound,
which method comprises the steps of:
 (a) contacting the sample with an antibody produced by immunization with an immunogen which includes as an antigenic determinant 6-aminihexyl-p-tolylacetamide, which antibody specifically binds to said first compound or said second compound; and
 (b) observing any binding of said antibody to an antigen in the sample,
wherein any such binding between said antibody and said antigen in the sample is indicative of the presence of said antigen.

7. A method according to claim 6 wherein a is not 0.
8. A method according to claim 6 wherein X is chlorine.
9. A method according to claim 7 wherein X is chlorine.
10. A method according to claim 6 wherein the first compound is trichloroethylene or perchloroethylene.

* * * * *